(12) United States Patent
Ullman

(10) Patent No.: US 6,447,799 B1
(45) Date of Patent: Sep. 10, 2002

(54) THROMBOPLASTIC SYSTEM

(76) Inventor: Joseph M. Ullman, 17 White Rock Dr., Falmouth, ME (US) 04105

( * ) Notice: Subject to any disclaimer, the term of this patent is extended or adjusted under 35 U.S.C. 154(b) by 16 days.

(21) Appl. No.: 09/670,451

(22) Filed: Sep. 26, 2000

Related U.S. Application Data

(60) Provisional application No. 60/220,405, filed on Jul. 24, 2000.

(51) Int. Cl.$^7$ .......................... A61L 15/32; A61M 35/00
(52) U.S. Cl. ................ 424/447; 128/DIG. 22; 604/290; 604/306
(58) Field of Search ............... 128/DIG. 22; 604/890.1, 604/1, 2, 3, 290, 304, 306, 307, 308; 424/443, 444, 445, 446, 447, 448, 449

(56) References Cited

U.S. PATENT DOCUMENTS

| | | | |
|---|---|---|---|
| 3,580,254 A | * 5/1971 | Stuart | 604/290 |
| 4,292,972 A | * 10/1981 | Pawelchak et al. | 604/368 |
| 4,363,319 A | * 12/1982 | Altshuler | 604/304 |
| 4,453,939 A | * 6/1984 | Zimmerman et al. | 604/368 |
| 4,899,739 A | * 2/1990 | Konishi | 604/306 |

* cited by examiner

*Primary Examiner*—Jeffrey E. Russel
(74) *Attorney, Agent, or Firm*—Pierce Atwood

(57) ABSTRACT

A thromboplastic system and related method for establishing hemostasis. The kit includes an absorptive pad, a thrombin retainer, and a non-stick backing. The absorptive pad may be a foam pad or a set of foam pads. The retainer may be a single bubble pack having the thrombin therein, or a set of bubble packs, one with thrombin and the other with a diluent. The retainer includes a breakable base, such as a foil base, that keeps the thrombin separate from the pad until forced open. When that happens, the thrombin moves into the pad to form a thrombin-soaked gelatin foam pad. The pad may then be applied to a wound. An applicator may be used to maintain uniform pressure on the pad over the wound.

14 Claims, 3 Drawing Sheets

THROMBOPLASTIC SYSTEM

CROSS-REFERENCE TO RELATED APPLICATION

This application claims the priority benefit of provisional application Ser. No. 60/220,405 filed Jul. 24, 2000, of the same title and by the same inventor.

BACKGROUND OF THE INVENTION

1. Field of the Invention

The present invention relates to systems for accelerating the clotting of blood. More particularly, the present invention relates to a foam pack kit for applying thrombin or a similar clotting agent to a wound.

2. Description of the Prior Art

Every week, 360,000 Americans undergo hemodialysis three (3) times a week. Most, if not all, of those patients have a tube under the skin to establish a fluid transfer path. In order to complete the flow path through the dialysis machine, two openings or wounds must be made in the patient in order to connect the tube to the machine. Specifically, the tube, sometimes referred to as a graft, connects an artery and vein. The connection, when pressurized, creates an artificial high-flow conduit that can be repeatedly punctured with large bore needles to allow dialysis. In many other cases, a surgical connection is established between the artery and vein. The surgical connection is known as a fistula. It accomplishes substantially the same function as the graft. Therefore, on the three-per-week dialysis schedule, each patient must be accessed through graft or fistula openings six times per week.

The graft and fistula structures function nearly at systemic blood pressure. Therefore, when they are removed, considerable bleeding occurs. Traditionally, fingertip pressure is applied by healthcare personnel, in some cases for a minimum of 10 minutes, and often longer, in order to stem the bleeding. Under repeated dialysis procedures, the fistula and grafts may not easily be re-opened in that they often become clotted or narrowed. It therefore becomes necessary to use larger bore needles and tubes to establish an appropriate fluid pathway. The larger wounds associated with these larger openings often translate into longer time periods to halt bleeding when the devices are removed.

Isolated efforts have been made to improve the hemostasis process. In one instance, the present inventor developed and employed in limited circumstances in some healthcare facilities, a system for that purpose. Initially, the effort involved simply applying a gelatin foam sponge to the wound site, with pressure, to accelerate hemostasis, or clotting, at the puncture site. This reduced the time to clotting, but the time required was still considerable. Recently, thrombin, a protein agent that accelerates clotting, was added to the sponge. The particular system involves cutting the sponge and applying to that sponge a mixture of the two components used to create the commercially available thrombin. The combination results in a gel-like solid structure that may be applied directly to the wound. The combination accelerates the clotting very well. In addition, a small square of a non-stick gauze pad, such as a Telfa™ pad, may be placed on the surface of the foam/thrombin combination to prevent unintended sticking of the foam prior to application to the wound.

Unfortunately, while the combination described above works well as a thromboplastic system, it is a jury-rig arrangement requiring as much or more time to make as it does to clot the blood using hand pressure. Moreover, there may be inconsistency in the amount of thrombin applied to the foam, the adequacy of the size of the foam pad, and the opportunity to forget the application of the non-stick pad. Therefore, what is needed is a ready-to-use system for conveniently and adequately establishing hemostasis, whether after a dialysis procedure or in regard to clotting any wound. Also, given the scope of the problem—many thousands of wounds daily throughout the world requiring clotting—such a system must be relatively inexpensive to obtain and relatively easy to use.

SUMMARY OF THE INVENTION

In view of the foregoing, it is an object of the present invention to provide a ready-to-use system for conveniently and adequately establishing hemostasis in a wound. It is also an object of the invention to provide such a thromboplastic system that is relatively inexpensive to obtain and relatively easy to use.

These and other objects are achieved with the present invention, which is a three-part kit for establishing hemostasis. The kit includes a pre-packaged combination of the sponge foam, pre-cut into an array of selectable sizes, to which the non-stick gauze is attached. A thrombin-containing device, such as a small blister or tear-through bubble pack, is included in the kit. It may be affixed to the side of the foam that is not coupled to the gauze. Alternatively, two small blisters or packets may be affixed to that side of the foam; one packet containing lyophilized (freeze-dried) thrombin and the other a thrombin diluent.

In the process associated with use of the present system to protect a wound, either the single thrombin-containing device is opened, or the two bubbles are pinched or pressed together and mixed. The thrombin or the thrombin/diluent mixture then enters the foam directly to create a gel/foam combination that may be applied directly to the wound. Pressure is then applied to the gauze side that does not stick to the pressure-applying structure. That structure may be a sterile stick or a healthcare provider's covered fingers.

The present invention eliminates the need to have three different products, the need to cut individual foam and gauze pieces, and the need to obtain and manipulate a thrombin bottle. It also eliminates the need to stick a syringe under sterile conditions into the bottle, pull it out, squirt the thrombin onto the foam, make a sandwich with the gauze and only after all that stick the combination on the wound. The present invention reduces supplies, waste, and accidental needle sticks. Given the cost of the individual components, the kit would be relatively inexpensive in comparison to the excess materials and healthcare provider's time involved in making each part.

In summary, the present invention is a self-contained small packet or kit with one or more pieces of an absorptive foam, one side of which is backed with a non-stick material, such as gauze, to reduce adherence on the opposing side, and one or more breakably sealed blisters on the other side. The blister or blisters are manipulated to activate the thrombin reagent and deliver it to the foam. The impregnated foam may then be applied to the wound site.

These and other advantages of the present invention will be understood upon review of the drawings, the detailed description, and the appended claims.

DETAILED DESCRIPTION OF PREFERRED EMBODIMENTS

Figure 1:
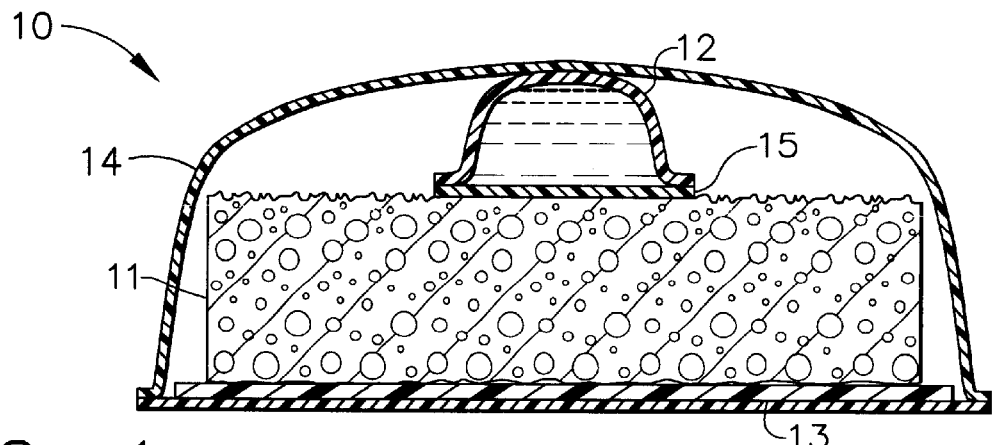
FIG. 1 is a side view of a simplified representation of a first embodiment of the thromboplastic system of the present invention, showing a single thrombin-retaining element.
Figure 2:
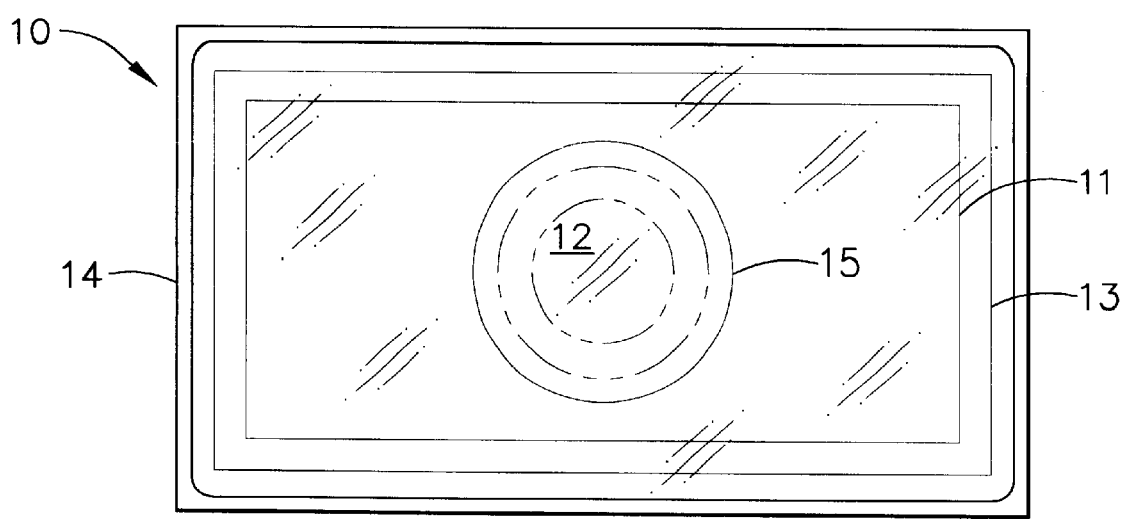
FIG. 2 is a top view of a simplified representation of the first embodiment of the thromboplastic system of FIG. 1.

A first thromboplastic system or kit 10 of the present invention is illustrated in FIGS. 1 and 2. The system 10 includes a thrombin receiving pad 11, a thrombin retainer 12, a pad backing 13, and a sealing pack 14 to hold the other parts therein in a sterile environment until ready for use. The pad 11 may be a gelatin foam pad, or a set of such pads, suitable for absorbing thrombin within the retainer 12 when the retainer 12 is broken open to release the thrombin onto and into the pad 11. The retainer 12 is preferably a plastic bubble pack including a foil or other suitable breakable sealing base 15 that is affixed to the pad 11. The sealing base 15 keeps the thrombin away from the pad 11 until the two are to be combined for use to seal a wound. When that occurs, a foam/gel pad is created for that purpose. The backing 13 includes first surface for attachment to the pad 11 and an opposing non-adherent or non-stick surface to contact a patient's skin. The backing 13 is affixed to the pad 11 on its surface opposite that of the retainer 12. The sealing pack 14 is of any type suitable for holding the contents therein in a sterile environment. One such type may be a retainer pack used to enclose sterile gauze pads or other retainers well known by those skilled in the healthcare field.

Figure 3:
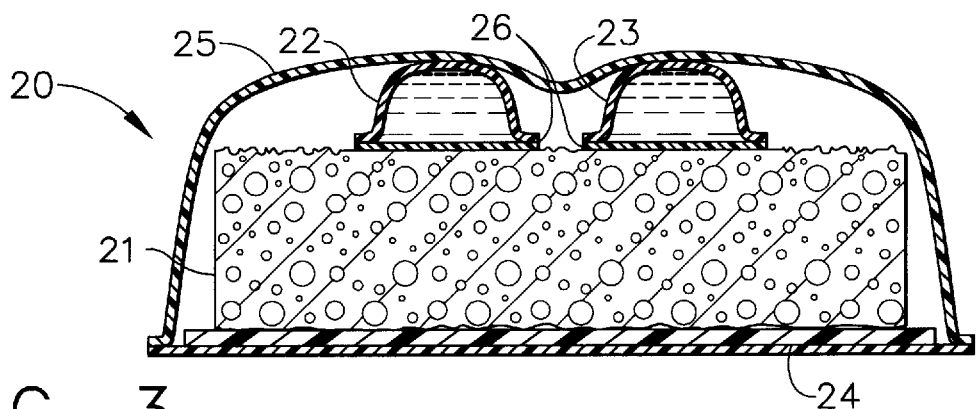
FIG. 3 is a side view of a simplified representation of a second embodiment of the thromboplastic system of the present invention, showing a thrombin-mixing packet element.
Figure 4:
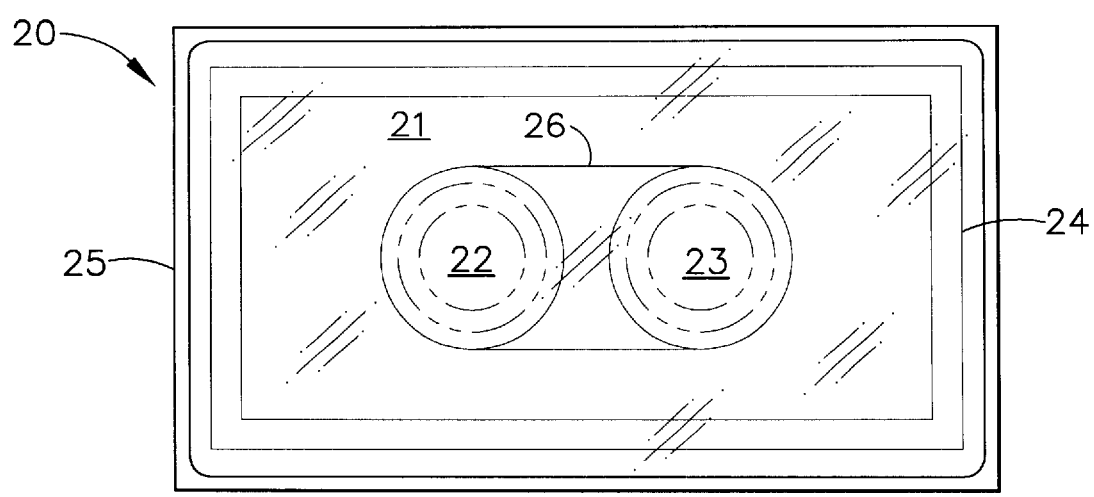
FIG. 4 is a top view of a simplified representation of the second embodiment of the thromboplastic system of FIG. 3.

A second embodiment of the present invention is shown in FIGS. 3 and 4. A second thromboplastic system or kit 20 of the present invention includes a thrombin receiving gelatin foam pad 21, a first thrombin component retainer 22, a second thrombin component retainer 23, a pad backing 24, and a sealing pack 25 to hold the other parts therein in a sterile environment until ready for use. As with the pad 11 of the first system 10, the pad 21 may be a sterile gelatin foam pad, or a set of such pads, suitable for absorbing thrombin when retainers 22 and 23 are broken open and combined to release onto and into the pad 21. The first and second retainers 22 and 23 are each plastic bubble packs that may include a common foil or other suitable breakable sealing base 26 that is affixed to the pad 21. It is to be understood that each of the retainers 22 and 23 is designed to isolate their respective contents from one another until those contents are intentionally to be combined together. The sealing base 26 keeps the thrombin components away from the pad 21 until the two are to be combined for use to seal a wound. When that occurs, a thrombin enriched gelatin pad is created. The backing 24 includes a first surface for attachment to the pad 21 and an opposing non-adherent or non-stick surface to contact a patient's skin. The backing 24 is affixed to the pad 21 on its surface opposite that of the retainers 22, 23. The sealing pack 25 is of any type suitable for holding the contents therein in a sterile environment. One such type may be a retainer pack used to enclose sterile gauze pads or other retainers well known by those skilled in the healthcare field.

Figure 5:
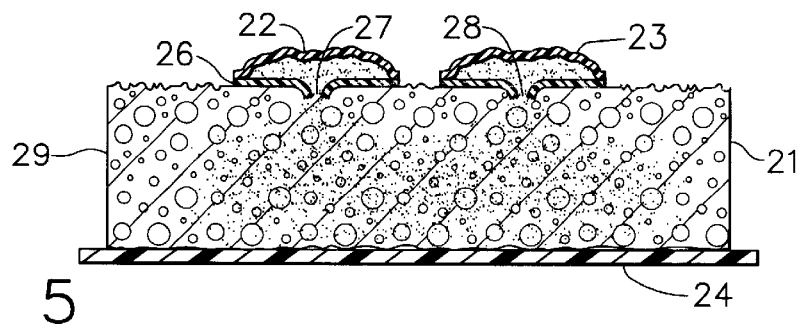
FIG. 5 is a side view of a simplified representation of the second embodiment of the thromboplastic system with the thrombin-mixing packet opened to deliver its contents into the thrombin-delivering foam gauze.
Figure 6:
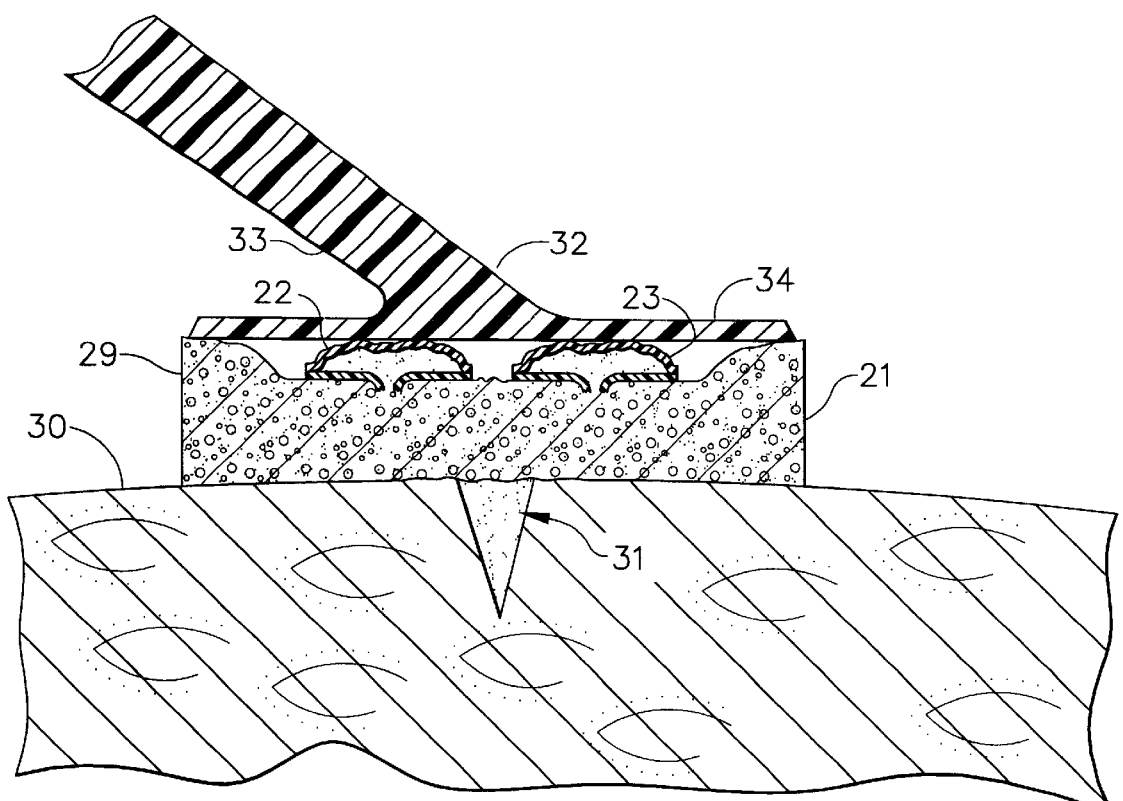
FIG. 6 is a side view of a simplified representation of the second embodiment of the thromboplastic system with the thrombin gel/foam gauze combination applied to a wound.

The method of the present invention for wound sealing using the foam/thrombin gel is fairly straightforward and involves steps associated with the stages of modification of system 20 represented in FIGS. 5 and 6. First, the healthcare provider presses downward on the two retainers 22 and 23 such that their contents force the sealing base 26 to open, such as at opening regions 27 and 28. The contents of the retainers 22 and 23, which may be lyophilized thrombin and a thrombin diluent, respectively, are then released into the pad 21. Massaging or other manipulation of the pad 21 forces a mixing of the two components together within the pad 21 and produces a thrombin enriched gel foam pad 29. The gel pad 29 is removed from the pack 25 and then applied on a patient's skin 30 over a wound 31, as shown in FIG. 6. The healthcare provider may leave the pad 29 in place, or may apply pressure to the wound 31 either by hand or with a uniform pressure applicator 32 having a handle 33 and a wide pressure plate 34. Although the method described has been presented with respect to use of the second system 20, it is to be understood that the same process is applicable with the single retainer 12 of the first system 10.

While the invention has been described with reference to a particular example embodiment, it is intended to cover all modifications and equivalents as described in the following claims.

What is claimed is:

1. A thromboplastic kit comprising:
   a. an absorptive pad having a first side and a second side;
   b. a thrombin retainer attached to said first side of said absorptive pad, wherein said thrombin retainer retains thrombin therein; and
   c. a non-stick backing attached to said second side of said pad.

2. The thromboplastic kit as claimed in claim 1 wherein said thrombin retainer is a plastic bubble pack.

3. The thromboplastic kit as claimed in claim 2 wherein said thrombin retainer further includes a breakable backing coupling said bubble pack to said first side of said absorptive pad.

4. The thromboplastic kit as claimed in claim 1 further comprising a sealing pack for retaining said pad, said thrombin retainer and said non-stick backing therein.

5. A thromboplastic kit comprising:
   a. an absorptive pad having a first side and a second side;
   b. a first thrombin component retainer attached to said first side of said absorptive pad, wherein said first thrombin component retainer retains thrombin therein;
   c. a second thrombin component retainer attached to said first side of said absorptive pad, wherein said second thrombin component retainer retains a thrombin diluent therein; and
   d. a non-stick backing attached to said second side of said pad.

6. The thromboplastic kit as claimed in claim 5 wherein said first thrombin component retainer and said second thrombin component retainer are plastic bubble packs.

7. The thromboplastic kit as claimed in claim 6 wherein said first thrombin component retainer and said second thrombin component retainer include a common breakable backing coupling both of said bubble packs to said first side of said absorptive pad.

8. The thromboplastic kit as claimed in claim 5 further comprising a sealing pack for retaining said pad, said first thrombin component retainer, said second thrombin component retainer, and said non-stick backing therein.

9. The thromboplastic kit as claimed in claim 5 wherein said thrombin is lyophilized thrombin.

10. A method for establishing hemostasis using a thromboplastic kit, the kit comprising an absorptive pad with a thrombin retainer means isolating thrombin from the absorptive pad, the method comprising the steps of:
   a. applying pressure to the thrombin retainer means to force thrombin to exit the thrombin retainer means and enter the absorptive pad;
   b. massaging the absorptive pad so that the thrombin and pad combine to form a thrombin-soaked pad; and
   c. applying said thrombin-soaked pad to a wound.

11. The method as claimed in claim 10 wherein the thrombin retainer means includes a retainer pack having thrombin therein.

12. The method as claimed in claim 10 wherein the thrombin retainer means includes a first thrombin component retainer pack having thrombin therein, and a second thrombin component retainer pack having a thrombin diluent therein.

13. The method as claimed in claim 12 wherein the thrombin is lyophilized thrombin.

14. The method as claimed in claim 10 further comprising the step of forcing said pad onto the wound with a pressure applicator.

* * * * *